United States Patent [19]

Benson et al.

[11] Patent Number: 5,094,838

[45] Date of Patent: Mar. 10, 1992

[54] AEROSOL HAIR SPRAY COMPOSITION

[75] Inventors: Alice B. Benson, Paterson; Joseph C. Hourihan, Little Falls, both of N.J.; Uma Tripathi, New Canaan, Conn.

[73] Assignee: Playtex Beauty Care, Inc., Stamford, Conn.

[21] Appl. No.: 571,767

[22] Filed: Aug. 29, 1990

[51] Int. Cl.$^5$ ................................................ A61K 7/11
[52] U.S. Cl. .......................................... 424/47; 424/71; 424/DIG. 1; 424/DIG. 2
[58] Field of Search ............... 424/47, 71, 78, DIG. 1, 424/DIG. 2

[56] References Cited

U.S. PATENT DOCUMENTS

| | | | |
|---|---|---|---|
| 3,684,776 | 8/1972 | Field et al. | 260/78.5 T |
| 3,684,777 | 8/1972 | Field et al. | 260/78.5 T |
| 3,721,655 | 3/1973 | Schlumbom et al. | 260/78.5 T |
| 3,836,637 | 9/1974 | Schmolka et al. | 424/70 |
| 3,862,306 | 1/1975 | Block et al. | 424/47 |
| 3,907,984 | 9/1975 | Calvert et al. | 424/47 |
| 3,922,341 | 11/1975 | Abegg et al. | 424/47 |
| 3,927,199 | 12/1975 | Micchelli et al. | 424/47 |
| 4,001,392 | 1/1977 | Curry et al. | 424/47 |
| 4,151,269 | 4/1979 | Torii et al. | 424/47 |
| 4,164,562 | 8/1979 | Nandagiri et al. | 424/47 |
| 4,192,862 | 3/1980 | Pengilly | 424/47 |
| 4,210,161 | 7/1980 | Wagman | 132/7 |
| 4,261,972 | 4/1981 | Nandagiri et al. | 424/47 |
| 4,315,910 | 2/1982 | Nowak, Jr. et al. | 424/47 |
| 4,520,008 | 5/1985 | Ando et al. | 424/47 |
| 4,842,852 | 6/1989 | Nowak, Jr. et al. | 424/71 |

OTHER PUBLICATIONS

Kirk—Othmer Encyclopedia of Chemical Technology 3rd ed. vol. 12, 1980 pp. 95–100.

*Primary Examiner*—Thurman K. Page
*Assistant Examiner*—Susan S. Rucker
*Attorney, Agent, or Firm*—Abelman Frayne & Schwab

[57] ABSTRACT

An aerosol hair spray composition which provides both significantly increased holding power and decreased drying time contains about 3.5% to about 5% of a lower alkyl ester of an alkyl vinyl ether maleic-acid copolymer, from 50% to 80% of a lower aliphatic alcohol, from 0.53% to about 0.72% of a neutralizing agent, from 25% to about 35% of a propellant and the aerosol spray is maintained at 30 to 50 lbs./sq. inch and delivered at a rate of 0.4 to 0.8 grams/sec. at 70° F.

5 Claims, No Drawings

AEROSOL HAIR SPRAY COMPOSITION

BACKGROUND OF THE INVENTION

1. Field of the Invention

This invention relates to an aerosol hair spray and, more particularly, to an aerosol hair spray which provides both increased holding power and decreased drying time.

2. Description of the Art

Aerosol hair sprays which deliver either high hold or a fast drying time are known in the art. While aerosol sprays having high holding power can be achieved by increasing the level of resin, such increase in resin level typically results in imparting an undesirable sticky/tacky feel to the hair and in possible clogging of the valve in the aerosol delivery system, notwithstanding compatability of the resin and propellant. While a decrease in drying time can be achieved by an increase in the level of the propellant employed in the aerosol, even if the propellant is compatible with the resin employed there is a propensity for the aerosol valve to become clogged.

While the art has recognized the need for an aerosol hair spray formulation possessed of both high holding power and fast drying time, its attainment has proven elusive since it is not simply a matter of balancing, but, rather, many interacting factors must be carefully considered, weighed and determined. Among the factors, but not limited thereto, are resin type and amount, type and level of propellant or mixture of propellants, the degree to which the resin is neutralized, the spray rate, and an appropriate aerosol delivery system. The latter refers to the various dimensions of an aerosol valve and its actuator.

SUMMARY OF THE INVENTION

It is an object of the present invention to provide an aerosol hair spray composition which provides both increased holding power and decreased drying time when compared with prior art compositions while eliminating the sticky and tacky feel usually associated with such type hair sprays.

It has now been found that the foregoing object, as well as other objects, can be achieved by employing an aerosol-hair spray composition which comprises:

(a) from about 3.5% to about 5.0%, by weight of a lower alkyl ester of an alkyl vinyl ether-maleic acid copolymer;

(b) from about 50% to about 80%, by weight, of an aliphatic two to three carbon alcohol;

(c) from about 0.53% to about 0.72%, by weight, of a neutralizing agent;

(d) from about 25% to about 35%, by weight, of a hydrocarbon propellant or mixture of propellants; and (e) said aerosol maintained at a pressure of about 30 to about 50 lbs./square inch at 70° F. and delivering an aerosol spray at the rate of about 0.4 to about 0.8 gram/second at 70° F.

DETAILED DESCRIPTION OF THE INVENTION

The resin employed in this invention is a copolymer of a lower alkyl ester, i.e., a one to four carbon atom alkyl ester, of alkyl vinyl ether-maleic acid copolymer. The copolymer thus has a repeating unit represented by the formula

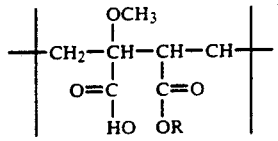

wherein R is an alkyl radical containing one to four carbon atoms. R is preferably ethyl or butyl and is most preferably ethyl.

Among the vinyl alkyl ethers useful in preparing the resins of the present invention may be mentioned methyl vinyl ether. These resins are well-known commodities of commerce and generally have molecular weights in the range of 20,000–80,000. The monoethyl ester of methyl vinyl ether-maleic acid copolymer is commercially available as Gantrez ES-225 and the butyl monoester of the methyl vinyl ether-maleic acid copolymer is commercially available as Gantrez ES-425, both of these products being available commercially as 50% solutions in ethanol. The polymers are not water-soluble. The resin is preferably neutralized to the extent of about 5% to about 25% of the free carboxyl groups by the addition of an organic base, for example, dimethyl stearamine, dimethyl-or diethyl-amine, triethanol-or triisopropanol amine, ammonia, aminomethyl propanol, aminomethyl propanediol and the like. Preferably, the resin in the aerosol hair spray formulation of the present invention is employed in an amount of about from about 3.5%, by weight, to about 5%, by weight, based on the total weight of the composition. It is especially preferred to employ from about 3.8% to about 4.6%, by weight, of the resin in the composition of the present invention. Most preferably, 4.2% of the resin is employed.

The alcohol employed in the composition is an aliphatic, two to three carbon atom, monohydric alcohol. Isopropanol and especially ethanol are preferred. The concentration of the alcohol in the composition is preferably about 50% to about 80%, by weight. It is especially preferred to employ from about 54% to about 74%, by weight, of the alcohol. Most preferably, 64.9%, by weight, of the alcohol is employed.

The propellant of the present invention is selected from the group consisting of straight chain or branched chain hydrocarbons having from 1 to 4 carbons atoms. It is preferred to employ a mixture of isobutane and propane wherein the percentage by weight of the mixture is from about 25% to about 35% of the weight of the hair spray composition. An especially preferred weight percentage is from 27% to 33%. 30%, by weight, of propellant is most preferred.

It has also been found that by delivering the aerosol hair spray at a rate of about 0.4 to 0.8 grams/second at 70° F. from a container under a pressure of about 30 psi to about 50 psi at 70° F., results in a hair spray composition which is neither too wet upon its application, nor does it become too sticky or tacky while drying. In addition, operating at a spray rate of 0.4 to 0.8 grams/second, or at the more preferred rate of 0.5 to 0.7 grams/second, prevents clogging of the valve/actuator assembly when employing the relatively high resin levels of the present invention.

The plasticizers of the present invention can include silicones, lanolin compounds, glycerine, etc. It is preferred to employ a mixture of phenyl trimethicone, lauramide DEA and Solulan 98, which is the brand name for a mixture of polysorbate 80, cetyl acetate and acetylated lanolin alcohol. Each of the three plasticizers is present in a quantity of from about 0.03% to about 0.05%, by weight. It is especially preferred to employ 0.04%, by weight, of each of the three (3) plasticizers.

Optional additives may be incorporated into the aerosol formulations of this invention in order to modify certain properties thereof. Among these additives may be included emollients, lubricants and penetrants; protein hydrolysates and other protein derivatives, ethylene oxide adducts and polyoxyethylene cholesterol; dyes, tints, and other colorants; and perfumes and fragrances.

In general, the formulation of the present invention can be prepared by merely dissolving the resin in the alcohol, adding the neutralizing agent as required, as well as any modifying agents, and then charging this "concentrate" into the aerosol container. The aerosol valve is then crimped in place and the propellant added.

The following examples further describe and demonstrate the preferred embodiments within the scope of the present invention. The Examples are given solely for the purpose of illustration and are not to be construed as limitations of the present invention, as many variations are possible without departing from its spirit and scope.

EXAMPLE 1

The following composition is representative of a formulation in accordance with the present invention.

| | |
|---|---|
| SD Alcohol 40 | 64.92 |
| Dimethyl Stearamine | 0.62 |
| Ethyl Ester of PVM/MA Copolymer | 4.20 |
| Lauramide DEA | 0.04 |
| Phenyl Trimethicone | 0.04 |
| Polysorbate 80 and Cetyl Acetate and Acetylated Lanolin Alcohol | 0.04 |
| Fragrance | 0.14 |
| Isobutane and Propane | 30.00 |
| | 100.00% |

EXAMPLE 2

The following composition is representative of a commercially available high-holding aerosol hair spray.

| TITLE | W/W % |
|---|---|
| SD Alcohol 40 | 71.02 |
| Isobutane and Propane | 25.00 |
| Ethyl Ester Of PVM/MA CoPolymer | 3.18 |
| Dimethyl Stearamine | 0.44 |
| Dimethicone Copolyol | 0.19 |
| Fragrance | 0.17 |
| | 100.00% |

EXAMPLE 3

The following composition is representative of another commercially available high-holding aerosol hair spray.

| TITLE | W/W % |
|---|---|
| SD Alcohol 40 | 70.81 |
| Aminomethyl Propanol | 0.53 |
| Octylacrylamide/Acrylates/Butyl- | 3.00 |

-continued

| TITLE | W/W % |
|---|---|
| Aminoethyl/Methacrylate/Copolymer | |
| Cetearyl Octanoate | 0.23 |
| Lauramide Dea | 0.08 |
| Phenyltrimethicone | 0.08 |
| Dimethicone Copolyol | 0.08 |
| Fragrance | 0.19 |
| Isobutane and Propane | 25.00 |
| | 100.00% |

EXAMPLE 4

The following composition is representative of still another commercially available aerosol hair spray claiming to be a high-holding, fast drying spray.

| TITLE | W/W % |
|---|---|
| SD Alcohol 40 | 69.10–70.53 |
| Isobutane and Propane | 25.00 |
| Ethyl Ester of PVM/MA Copolymer | 3.35 |
| Isostearamidopropyl Dimethylamine | 0.10–0.50 |
| Panthenol | 0.10–0.50 |
| Aminomethyl Propanol | 0.50 |
| Ethyldihydroxypropyl PABA | 0.10–0.50 |
| Polysorbate 80 | 0.05–0.1 |
| Cetyl Acetate | 0.05–0.1 |
| Acetylated Lanolin | 0.05–0.1 |
| Fragrance | 0.17–0.25 |
| | 100.00% |

COMPARATIVE DATA

The hair holding properties of the four (4) formulations of Examples 1–4, inclusive, were evaluated pursuant to the standard High Humidity Curl Retention Test described at page 432 of "The Aerosol Handbook", 2nd edition, published by Wayne Dorland Co. The evaluation was conducted at 72° F. and 90% relative humidity (R.H.). Readings were taken at 4 hours.

In addition, each of the formulations of Examples 1–4 were also evaluated for their drying times in the salon on patrons. Dry time is calculated by the following formula:

$$\text{Dry Time (seconds/g. resin)} = \frac{(T)}{(W_1) - (W_2)} \div \text{Parts of Resin Solids In Products}$$

$W_1$ = weight of aerosol can prior to spraying
$W_2$ = weight of aerosol can after spraying
$T$ = amount of time immediately after completion of spraying until complete dryness is achieved.

Dry time evaluations on the formulations of Examples 1–4 yielded the following results recorded in Table 1 below. HHCR is an average of seven readings, while dry time is an average of six readings.

TABLE 1

| Example | HHCR @ 4 Hrs | Dry Time sec./g. resin |
|---|---|---|
| 1 | 86.5% | 486 |
| 2 | 76.0% | 642 |
| 3 | 72.7% | 530 |
| 4 | 21.1% | 460 |

From the foregoing it is readily evident that the formulation of the present invention, namely, the formulation of Example 1, had significantly greater holding power, at a 95% confidence level, when compared with the commercially available high hold aerosol spray formulations of Examples 2-4.

The results also establish that the composition of the present invention had a dry time comparable to or better than the formulations of Examples 2-4.

Thus, the aerosol hair spray composition of the present invention is seen to posses the combinations of both superior holding power and decreased drying time when compared with commercially available aerosol hair sprays.

It will be appreciated that various changes can be made in the composition of the present aerosol hair spray formulation and in its use without departing from the spirit and scope of the present invention. The various embodiments which have been described herein were intended to further illustrate the invention, but were not intended to limit it.

What is claimed is:

1. An aerosol hair spray for styling and holding the hair, consisting essentially of:
   a) from about 3.5% to about 5.0%, by weight, of a lower alkyl ester of alkyl vinyl ether maleic acid copolymer;
   b) from about 50% to about 80%, by weight, of an aliphatic 2 to 3 carbon atom monohydric alcohol;
   c) from about 0.53% to about 0.72%, by weight, of an organic amine base as a neutralizing agent;
   d) from about 0.09% to about 0.15%, by weight, of a plasticizer or a mixture of plasticizers;
   e) from about 25% to about 35%, by weight, of a propellant, selected from the group consisting of straight or branched chain hydrocarbons having from 1 to 4 carbon atoms, or mixtures thereof, and
   f) said aerosol maintained at a pressure of about 30 pounds to about 50 pounds per square inch at 70° F. and delivering an aerosol spray at the rate of about 0.4 to about 0.8 grams/second at 70° F.

2. The aerosol hair spray composition of claim 1 in which the lower alkyl ester is the monoethyl ester of methyl vinyl ether maleic acid copolymer, the alcohol is ethanol and the propellant is a mixture of isobutane and propane.

3. The aerosol spray composition of claim 2, in which the quantity of the monoethyl ester of methyl vinyl ether maleic acid copolymer is about 3.8% to about 4.6%, by weight, the quantity of ethanol is about 54% to about 74%, by weight, and the quantity of the isobutane-propane mixture is about 27% to about 33%, by weight.

4. The aerosol hair spray composition of claim 1 in which the organic amine base is dimethyl stearamine.

5. The aerosol hair spray composition of claim 3 in which the aerosol is delivered at a spray rate of about 0.5 to about 0.7 grams/second at 70° F.

* * * * *